United States Patent
Ahn et al.

(10) Patent No.: US 11,253,619 B2
(45) Date of Patent: Feb. 22, 2022

(54) ULTRAVIOLET STERILIZER

(71) Applicant: POINT ENGINEERING CO., LTD., Asan (KR)

(72) Inventors: Bum Mo Ahn, Suwon (KR); Seung Ho Park, Hwaseong (KR); Moon Hyun Kim, Asan (KR)

(73) Assignee: POINT ENGINEERING CO., LTD., Asan (KR)

( * ) Notice: Subject to any disclaimer, the term of this patent is extended or adjusted under 35 U.S.C. 154(b) by 0 days.

(21) Appl. No.: 16/890,777

(22) Filed: Jun. 2, 2020

(65) Prior Publication Data
US 2020/0384139 A1 Dec. 10, 2020

(30) Foreign Application Priority Data
Jun. 7, 2019 (KR) .................. 10-2019-0067555

(51) Int. Cl.
*A61L 2/10* (2006.01)
*A61L 2/26* (2006.01)

(52) U.S. Cl.
CPC ........ *A61L 2/10* (2013.01); *A61L 2/26* (2013.01); *A61L 2202/11* (2013.01); *A61L 2202/121* (2013.01)

(58) Field of Classification Search
None
See application file for complete search history.

(56) References Cited

U.S. PATENT DOCUMENTS

| 8,980,622 | B2* | 3/2015 | Smith | C12Q 1/22 435/287.4 |
| 9,943,617 | B1* | 4/2018 | Burchman | C02F 1/325 |
| 10,139,305 | B2* | 11/2018 | Salg | A61L 2/10 |
| 2007/0057197 | A1* | 3/2007 | Chor | A61L 2/10 250/455.11 |
| 2010/0170104 | A1* | 7/2010 | Shami | A45D 20/12 34/283 |
| 2012/0006995 | A1* | 1/2012 | Greuel | A61L 2/10 250/373 |
| 2014/0319375 | A1* | 10/2014 | Nelson | A61L 2/025 250/455.11 |
| 2017/0119145 | A1* | 5/2017 | Munoz | F26B 3/04 |

FOREIGN PATENT DOCUMENTS

| KR | 20-0310601 | * | 4/2003 |
| KR | 10-2012-0037057 | A | 4/2012 |
| KR | 10-2013-0002573 | * | 1/2013 |
| KR | 10-2013-0002573 | A | 1/2013 |
| KR | 20-2013-0002604 | | 5/2013 |
| KR | 101801804 | B1 | 11/2017 |
| KR | 101905466 | B1 | 10/2018 |

* cited by examiner

*Primary Examiner* — Andrew Smyth

(57) ABSTRACT

Provided is a UV sterilizer including an illumination unit, a cover that has an open hole in an upper surface thereof and supports the illumination unit, and a body that is provided underneath the cover and secures an illumination distance between the illumination unit and an illumination target object. The body is composed of a first body and a second body into which the first body is inserted. The first body and the second body are separably combined with each other.

5 Claims, 7 Drawing Sheets

ULTRAVIOLET STERILIZER

CROSS REFERENCE TO RELATED APPLICATION

The present application claims priority to Korean Patent Application No. 10-2019-0067555, filed Jun. 7, 2019, the entire contents of which is incorporated herein for all purposes by this reference.

BACKGROUND OF THE INVENTION

Field of the Invention

The present invention relates to a UV sterilizer for killing harmful bacteria using UV light.

Description of the Related Art

Electronic products, such as computer keyboards, mice, and mobile phones, that are frequently used in everyday life, and mattresses and bedding items, such as duvets, that are used for sleeping cannot prevent growth of bacteria due to sweat or secretions from a human body. In addition, objects used or installed in public institutions are used by an unspecified number of people. Because of this, bacteria that cause various diseases grow more actively.

For sanitary reasons, the importance of a device for sterilizing an object has increased. Sterilizers using ultraviolet (UV) radiation are widely used to sterilize an object.

These UV sterilizers are disclosed in Korean Patent Nos. 10-1801804 and 10-1905466.

In Korean Patent No. 10-1801804, a sterilizer includes a central housing, two wing housings, and two UV lamps that are accommodated in the respective wing housings. The wing housings are connected to the central housing in a manner that is rotatable with respect to the central housing and is lengthwise-connectable to the central housing. In addition, the wing housings are connected to the central housing in such a manner as to rotate by an angle of 90 degrees with respect to the central housing. The length of the wing housing is adjusted in a manner that corresponds to the size of a mattress. Sterilization is performed during movement of the sterilizer along a lengthwise direction of the mattress.

In Korean Patent No. 10-1905466, a sterilizer includes a body, an infrared radiation unit, an article-clipping portion with which a sterilization target object is clipped, an ultraviolet radiation unit, a clip detection unit, and the like.

The sterilizer with this configuration sterilizes sterilization target objects, such as a mask, a handkerchief, and a wallet. For sterilization with the sterilizer, first, the sterilization target object is folded. The ultraviolet radiation unit is inserted, toward the closed edge of the folded sterilization target object, into a space formed by folding the sterilization target object. The open edge of the sterilization target object is clipped with the article-clipping portion.

Then, the clip detection unit detects the sterilization target object being clipped on the body. An LED of the ultraviolet radiation unit is turned on. Thus, the sterilization target object is sterilized.

In this manner, for the purpose of sterilizing a specific sterilization target object, the UV sterilizer has a structure suitable for the size of the specific sterilization. Therefore, objects that can be sterilized are limited. In other words, the UV sterilizer in the related art can sterilize objects having limited sizes. Thus, products having various sizes are difficult to sterilize. In order to sterilize products having various sizes, UV sterilizers have to be secured that can accommodate such products.

SUMMARY OF THE INVENTION

An objective of the present invention is to provide a UV sterilizer that is capable of sterilizing products having various sizes regardless of the sizes thereof and of effectively sterilizing the products at an improved uniformity ratio of illumination.

According to an aspect of the present invention, there is provided a UV sterilizer including: an illumination unit; a cover that has an open hole and supports the illumination unit; and a body that is provided underneath the cover and secures an illumination distance between the illumination unit and an illumination target object, in which the body includes a first body and a second body into which the first body is inserted, and the first body and the second body are separably combined with each other.

In the UV sterilizer, the first body and the second body may be separated from each other and may be selectively provided underneath the cover.

In the UV sterilizer, the first body may include a leg portion that extends longer than the other portions, and with the leg portion, the first body may be supported on a support and may secure the illumination distance.

In the UV sterilizer, a sealed sterilization space may be formed by flank surfaces of the second body and the cover, within the body.

In the UV sterilizer, the cover may include a nesting portion within which the illumination unit is nested.

According to the UV sterilizer according to the present invention, which is described above, the following advantages are provided.

The UV sterilizer employs a structure suitable in terms of portability and mobility and can effectively perform sterilization. In addition, products having various sizes, which are sterilization target objects, can be sterilized regardless of the sizes thereof. In addition, the UV sterilizer employs a structure for achieving a high uniformity ratio of illumination and can effectively sterilize an illumination target object.

DETAILED DESCRIPTION OF THE INVENTION

The following description exemplifies only the principle behind the invention. Therefore, although not explicitly described or illustrated in the present specification, various apparatuses that are predicted from the principle behind the invention and fall within the concept and scope of the invention will be apparent to a person of ordinary skill in the art. In addition, terms and embodiments that will be used and described, respectively, throughout the present specification are all intended primarily to help understand the concept of the present invention, and therefore it should be understood that the present invention is not limited to the terms and embodiments that are explicitly given with this intention.

Features and advantages of the present invention, which are described above, will be clearly understood from the following description with reference to the accompanying drawings, and thus the technical idea of the present invention will be easily embodied by a person of ordinary skill in the art to which the invention pertains.

In the present specification, embodiments of the present invention will be described with reference to exemplary cross-sectional and/or perspective diagrams. An embodiment of the present invention is not limited to a specific shape that is illustrated, and varies in shape according to a manufacturing process.

A UV sterilizer according to a preferable embodiment of the present invention will be described below with reference to the accompanying drawings.

Figure 1:
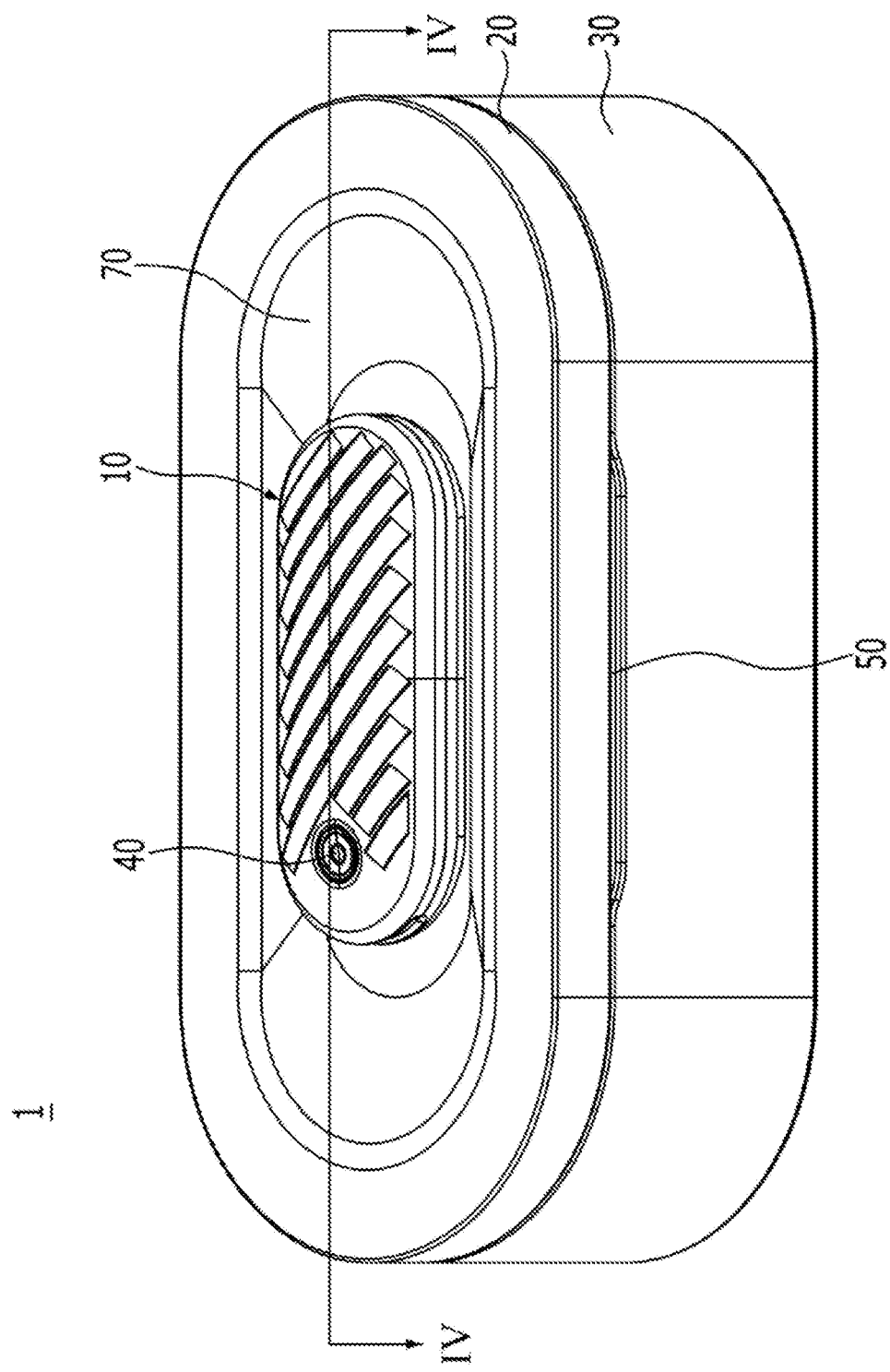
FIG. 1 is a diagram illustrating a UV sterilizer according to a preferable embodiment of the present embodiment.
Figure 2:
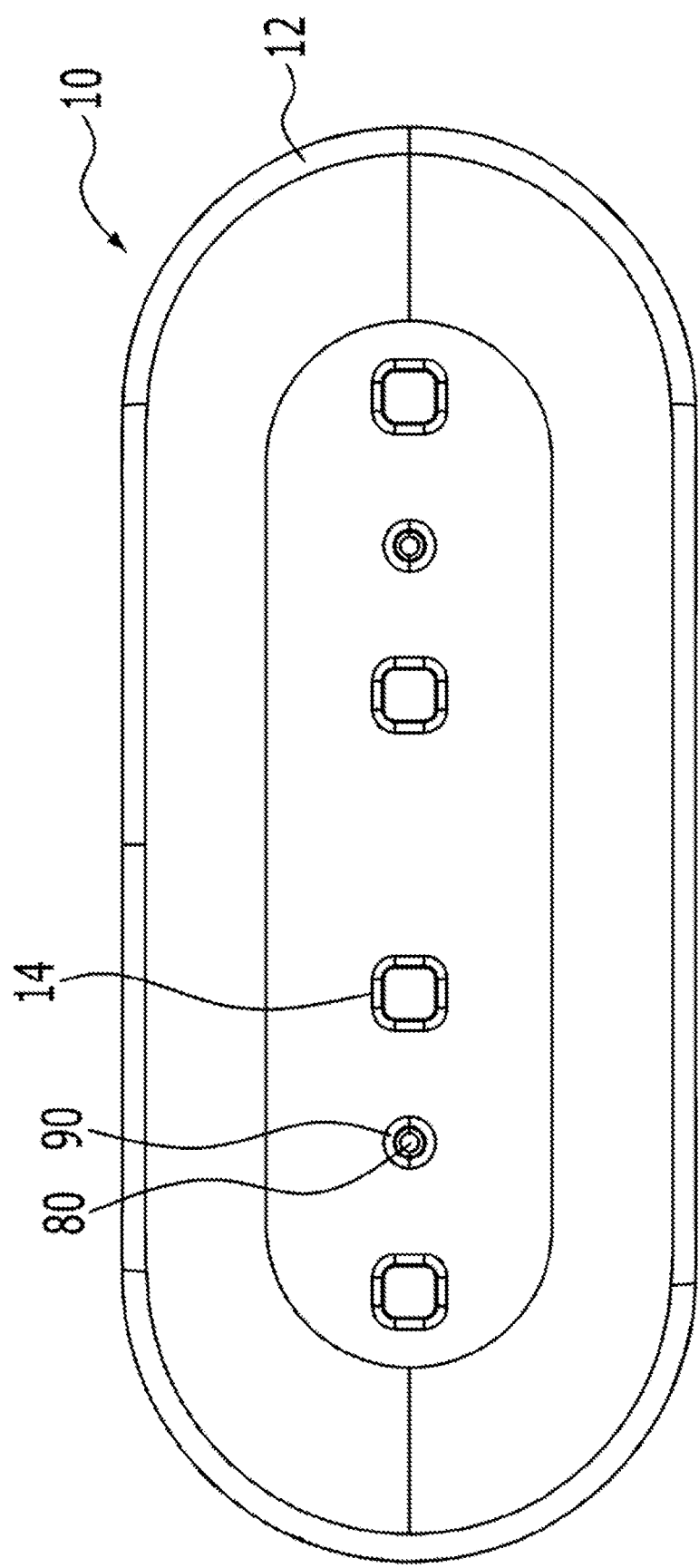
FIG. 2 is a diagram illustrating an illumination unit when viewed from below.
Figure 3:
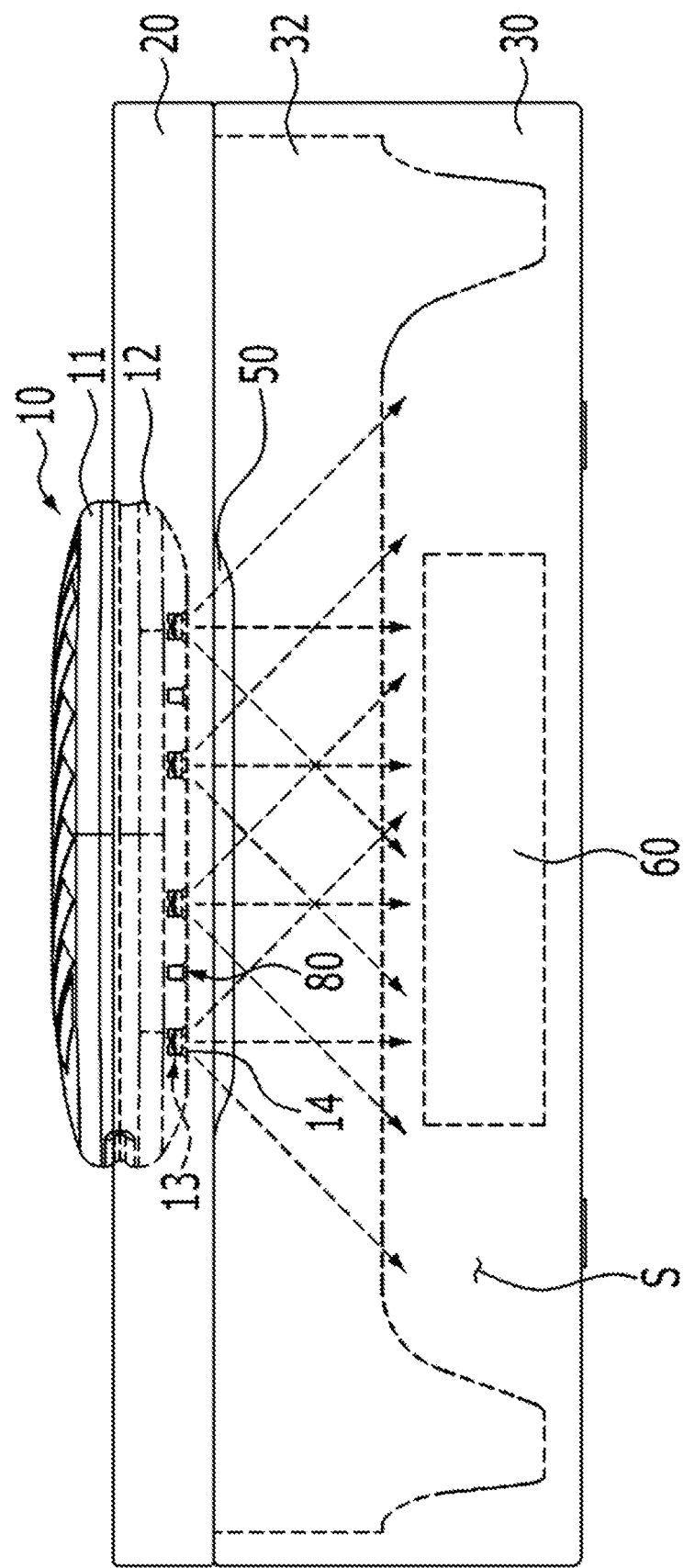
FIG. 3 is a diagram illustrating the UV sterilizer when viewed from the side.
Figure 4:
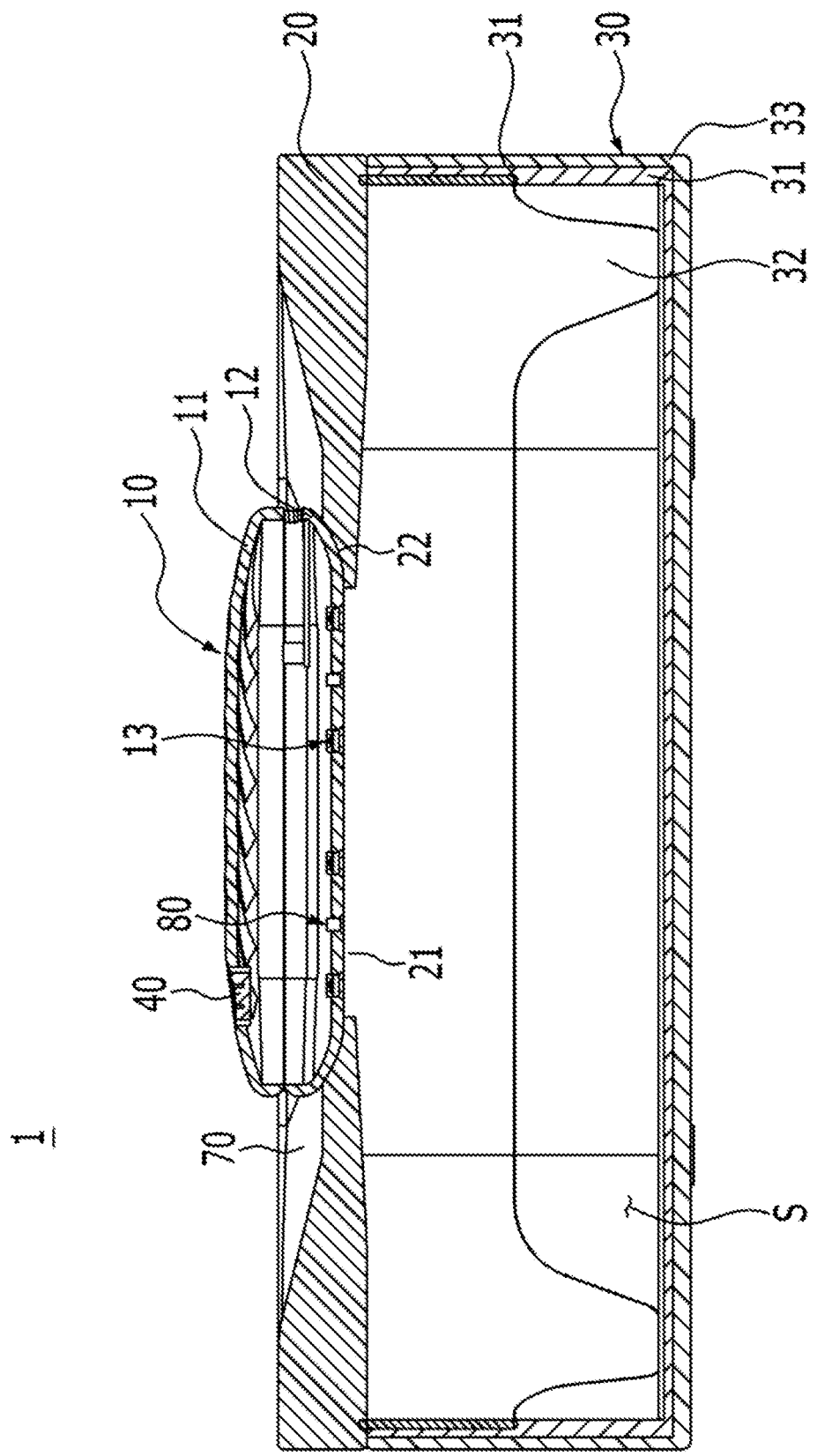
FIG. 4 is a diagram illustrating the UV sterilizer taken along line IV-IV in FIG. 1.
Figure 5:
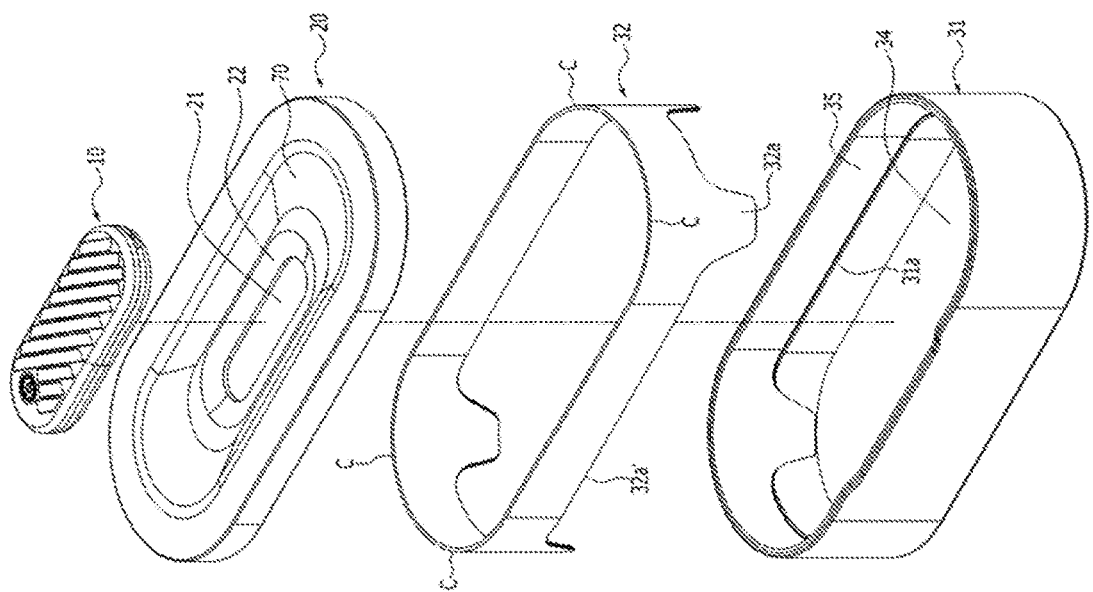
FIG. 5 is an exploded diagram illustrating the UV sterilizer according to the present invention.

FIG. 1 is a diagram illustrating the UV sterilizer according to the preferable embodiment of the present embodiment. FIG. 2 is a diagram illustrating an illumination unit when viewed from blow. FIG. 3 is a diagram illustrating the UV sterilizer when viewed from the side. FIG. 4 is a diagram illustrating the UV sterilizer taken along line IV-IV in FIG. 1. FIG. 5 is an exploded diagram illustrating the UV sterilizer. As illustrated in FIG. 1, a UV sterilizer 1 according to the present invention includes a illumination unit 10, a cover 20 that has an open hole 21 in an upper surface thereof and supports the illumination unit 10, and a body 30 that is provided underneath the cover 20 and secures an illumination distance between the illumination unit 10 and an illumination target object 60.

The illumination unit 10 includes: a UV LED 13 that causes UV light and a power supply unit that includes a power switch 40 and a power supply connector. As illustrated in FIG. 1, the power switch 40, for example, is configured to have a push button, but is not limited to this configuration.

The illumination unit 10 includes an upper body 11 and a lower body 12 that is combined with the upper body 11 with the lower body 12 underneath the upper body 11. In this case, an insertion hole to accommodate the power switch 40 is formed in the upper body 11, and a nesting recess for nesting the UV LED 13 is formed in the lower body 12.

For combination, the upper body 11 and the lower body 12 have the respective sizes corresponding to each other. A recess is formed, in the depth direction, in at least a portion of a combination surface of at least one of the upper body 11 and the lower body 12. This recess forms the power supply connector in a state where the upper and lower bodies 11 and 12 are combined. The power supply connector has a size that corresponds to a size of a cross section of a power supply cable.

As illustrated in FIG. 1, the insertion hole through which the power switch 40 is exposed to the outside is formed in the upper body 11. Accordingly, in a case where the power switch 40 is provided, at a position corresponding to the insertion hole, within the illumination unit 10, an upper surface of the power switch 40 is exposed to the outside. As an example, in a case where the power switch 40 is provided in the form of a cylinder, the insertion hole is formed in such a manner as to have the same diameter as the power switch 40.

The nesting recess 14 for nesting the UV LED 13 within the illumination unit 10 is formed in the lower body 12. Specifically, with reference to FIG. 2, the illumination unit 10 includes a plurality of UV LEDs 13. Accordingly, a plurality of nesting recesses 14 is formed in a lower surface of the lower body 12. Each of the nesting recess 14 is open at a lower end thereof that is flush with a lower surface of the lower body 12. The size of the lower end of each nesting recess 14 is smaller than the size of a transverse section of a corresponding one of the UV LEDs 13. Thus, the UV LEDs 13 are nested in the respective nesting recesses 14 while being mounted on the lower body 12.

Preferably, the UV LED 13 to be provided within the lower body 12 is a UV-C LED. The UV-C LED is provided within the lower body 12 and emits UV-C light in a wavelength range of 100 to 280 nm. The illumination target object 60 is sterilized with UV-C light.

As illustrated in FIG. 2, the illumination unit 10 includes multiple UV LEDs that are arranged a fixed distance apart. Accordingly, UV light that is emitted from the UV LED 13 is distributed within the illumination distance, and thus a sterilization area is uniformly formed. As a result, the illumination target object 60 is uniformly sterilized.

An auxiliary LED 80 is provided between each of the UV LEDs 13 arranged at intervals in the illumination unit 10. Therefore, multiple nesting recesses 14 within which UV LEDs 13, respectively, are nested are formed a distance apart in the lower body 12. An auxiliary LED nesting recess 90 within which the auxiliary LED 80 is nested is formed between each of the nesting recesses 14 that are arranged a distance apart. The auxiliary LED 80 is provided within the auxiliary LED nesting recess 90. Thus, when operating the UV sterilizer 1, through the opening portion 50, it can be checked with the naked eye whether or not the UV sterilizer 1 operates. Therefore, the auxiliary LED 80 is an LED that creates a wavelength range that is identifiable with the naked eye. Examples of the auxiliary LED 80 include a visible light LED and a UV-A LED.

Preferably, the visible light LED, when provided as the auxiliary LED 80, is a blue LED. The blue LED emits visible light in a wavelength range of 440 to 460 nm and thus is easily identifiable with the naked eye.

On the other hand, the UV-A LED, when provided as the auxiliary LED 80, emits UV-A light in a wavelength of 315 to 400 nm and the emitted UV-A light is identifiable with the naked eye.

The human eye detects light in a wavelength range of 400 to 700 nm. Therefore, light from the auxiliary LED 80 that is provided within the UV sterilizer 1 is easily identified with the naked eye.

Specifically, the UV sterilizer 1 according to the present invention sterilizes the illumination target object 60 using UV-C light emitted from the illumination unit 10. Through the opening portion 50 present between the cover 20 and the body 30, it is checked whether or not the UV sterilizer 1 performs UV sterilization. With reference again to FIG. 1, when combining the cover 20 and the body 30, the opening portion 50 is formed by a recess that is formed, in the depth direction, in at least a portion of a combination surface of one of the cover 20 and the body 30. According to the present invention, the opening portion 50 is provided as a gap between the cover 20 and the body 30. Thus, the light emitted from the auxiliary LED 80 within the UV sterilizer 1 can be identified with the naked eye because the light leaks through the opening portion 50. From the outside, it can be easily checked whether or not the UV sterilizer 1 operates.

The illumination unit 10 is formed to have a curved surface. Therefore, a surface of the illumination unit 10 has a curvature.

As illustrated in FIG. 3, the illumination unit 10 is supported on an upper surface of the cover 20. In this case, the cover 20 includes a nesting portion 22 within which the illumination unit 10 is nested and a concave portion 70 that is formed in the vicinity of the nesting portion 22.

With the nesting portion 22, the illumination unit 10 is supported on the upper surface of the cover 20.

The nesting portion 22 is concavely formed in the upper surface of the cover 20. Accordingly, the nesting portion 22 is formed to have an internal flank surface of which a surface curvature corresponds to a surface curvature of the illumination unit 10.

The nesting portion 22 serves to guide the illumination unit 10 to a position at which the illumination unit 10 has to be positioned on the upper surface of the cover 20. When the illumination unit 10 is positioned at a wrong position, UV light is emitted in a direction other than the direction of the illumination target object 60. With the nesting portion 22, this problem can be accordingly prevented. Thus, nonuniform sterilization of the illumination target object 60 and a decrease in uniformity ratio of illumination within the body 30 can be solved. In addition, the nesting portion 22 is brought into contact with a lower surface of the illumination unit 11, and thus UV light generated in the illumination unit 11 is prevented from being emitted to the outside.

The concave portion 70 formed to have a tapered surface is provided in the vicinity of the nesting portion 22. With reference to FIG. 4, the concave portion 70 is formed in the vicinity of the nesting portion 22 in a manner that is connected to the nesting portion 22. The concave portion 70 is formed to have a tapered surface. Thus, the more the nesting portion 22 is approached for connection, the smaller a width of the concave portion 70. Accordingly, a smooth connection to the nesting portion 22 is made.

With the concave portion 70 formed in the vicinity of the nesting portion 22, the illumination unit 10 to be nested within the nesting portion 22 is guided smoothly into the nesting portion 22 in an easy manner. In other words, the concave portion 70 serves to smoothly guide the illumination unit 10 to a position at which the illumination unit 10 has to be positioned within the nesting portion 22. Thus, the illumination unit 10 is guided to the position at which the illumination unit 10 has to be positioned within the nesting portion 22.

The cover 20 has the open hole 21 for distributing, toward the downward direction, UV light emitted from the illumination unit 10 nested within the nesting portion 22. The open hole 21 is formed in the upper surface of the cover 20, but in such a manner that the nesting portion 22 is provided in the vicinity thereof. In other words, a curved surface that forms the nesting portion 22 is formed in the vicinity of the open hole 21.

The open hole 21 is formed at a position corresponding to an area where a UV LED is present, of the illumination unit 10 nested within the nesting portion 22. At this point, the area where a UV LED is present means an area where a UV LED is present, which is created by the UV LED 13 being nested within each of the multiple nesting recesses 14 in the lower body 12 of the illumination unit 10. According to the present invention, UV light is emitted toward a fixed position through the open hole 21. Accordingly, when placing the illumination target object 60 within the body 30, a position at which the illumination target object 60 is to be placed is suitably selected. Thus, uniform sterilization is performed more effectively.

With this structure, UV light is emitted from the UV LED 13 in the illumination unit 10 into the body 30 provided underneath the cover 20.

As illustrated in FIG. 3, the body 30 is provided underneath the cover 20. In this case, the body 30 is separably combined with the cover 20, with the body 30 underneath the cover 20.

The body 30 is combined with the cover 20 in such a manner that at least a portion of the body 30 is inserted into a recess formed in the cover 20. The removable structure is not limited to this insertion structure. In a case where the cover 20 and the body 30 are combined with each other using the insertion structure, a protrusion is formed at a position that corresponds to a position of a recess formed in the cover 20. In this case, at least a portion of the cover 20, which is inserted into the recess in the body 30, is the protrusion.

UV light is emitted from the illumination unit 10 nested within the nesting portion 22 into the body 30 provided underneath the cover 20. An arrow that is illustrated in FIG. 3 indicates a direction in which UV light is emitted from the UV LED 13 in the illumination unit 10. In addition, an example of the illumination target object 60 is illustrated in FIG. 3. The illumination target object is not limited to a specific abject. In addition, the illumination target object 60 is not limited in size. The illumination target object 60 may be a product having a fixed size or an area in a fixed range.

The body 30 that is formed to a fixed height is provided underneath the cover 20, and thus secures the illumination distance between the illumination unit 10 and the illumination target object 60. In other words, in a case where the body 30 that is formed to a fixed height is provided underneath the cover 20, the illumination distance is secured between the illumination unit 10 and the illumination target object 60. Accordingly, the UV sterilizer can achieve an improvement in uniformity ratio of illumination.

Specifically, the body 30 is formed in the form of a box that is open at the top.

When the cover 20 is provided on the top of the body, UV light is accordingly emitted from the illumination unit 10 nested within the cover 20 into the body 30. The illumination target object 60, when placed within the body 30, is sterilized with UV light that is emitted.

In this case, the height of the body 30 makes it possible to secure the illumination distance between the illumination unit 10 and illumination target object 60. UV light that is emitted within the illumination distance is distributed, thereby increasing the uniformity ratio of illumination. The inside of the body 30 is sterilization space S where sterilization is performed, and UV light is distributed over the illumination distance secured by the body 30, thereby increasing the uniformity ratio of illumination.

UV light that is distributed over the illumination distance forms a sterilization area, and the uniformity ratio of illumination of the sterilization area is improved due to the illumination distance secured by the body 30.

In the case of sterilization using UV light, the higher the uniformity ratio of illumination, the more effectively the illumination target object 60 is sterilized. The sterilizer 1 directly illuminates the illumination target object 60 with UV light, and the illuminated illumination target object 60 is sterilized with UV light. Then, although multiple UV LEDs 13 are provided, when a sufficient illumination distance is not secured sufficiently, a distance over which UV light emitted from the UV LED 13 is distributed is not sufficient. Thus, only a portion of the illumination target object 60 is intensively illuminated with UV light. Accordingly, the uniformity ratio of illumination is decreased, and consequently, the illumination target object 60 is not properly sterilized.

However, according to the present invention, the body 30 is formed to a fixed height, and thus the illumination distance is secured between the illumination unit 10 and the illumination target object 60, thereby forming a structure for improving the uniformity ratio of illumination. Accordingly, only a portion of the illumination target object 60 can be prevented from being intensively illuminated with UV light, and the effect of uniformly sterilizing the illumination target object 60 can be achieved.

As illustrated in FIG. 4, the body 30 includes a first body 32 and a second body 31 into which the first body 32 is inserted, and further includes a housing 33 into which the second body 31 is inserted. The first body 32 and the second body 31 are separably combined with each other. For combination, the second body 31 is also separably inserted into the housing 33 that is selectively provided.

As illustrated in FIG. 4, regarding the structure of the UV sterilizer 1 according to the present invention, the first body 32 and the second body are combined in a manner that the first body 32 is inserted into the second body 31, thereby forming the body 30. The illumination target object 60 is placed within the body 30 so that the illumination target object 60 can be sterilized.

Alternatively, the first body 32 and the second body 31 may be separated from each other and may be selectively provided underneath the cover 20.

The first and second bodies 32 and 31 are described in detail with reference to FIGS. 4 and 5.

As illustrated in FIGS. 4 and 5, the first body 32 has longer portions 32a and shorter portions 32a'.

In the description hereinafter, the longer portions 32a and the shorter portions 32' that are named in terms of dimensions are also respectively referred to as leg portions 32a and non-leg portions 32a' that are named in terms of functions thereof. With the respective leg portions 32 that are in contact with the surface of a support at the lower ends thereof, the first body 32 is stably supported and the illumination distance is secured. In a case where only the first body 32 is provided underneath the cover 20, the illumination distance can be secured by the leg portions 32a, and thus the illumination target object 60 can be effectively sterilized at a high uniformity ratio of illumination.

As illustrated in FIG. 5, the first body 32 has an elliptical cross section that corresponds to an elliptical cross section of the cover 20. The first body 32 is open at the top and bottom and has four corner portions C.

The four corner portions C correspond to the leg portions 32a, respectively. Since the first body 32 has four corner portions C, the number of the leg portions 32a is also four. Alternatively, the leg portions 32a may be positioned at non-corner portions C. The term "non-corner portions" refers to portions other than the corner portions of the first body 32. That is, since it is required for the leg portions 32 only that they function as pillars that support an overlying object, the positions of the leg portions 32a are not particularly limited. As long as the first body 32 can be stably supported on a planar surface, the leg portions 32a may be provided at any positions of the first body 32. The leg portions 32 are not limited in position.

In other words, the first body 32 is composed of the leg portions 32a provided at the corner portions C and the non-leg portions 32a' provided at the non-corner portions C (which can be referred to as flank portions). Since there is a high difference between the leg portion 32a (i.e., corner portion C) and the non-leg portion 32a' (i.e., non-corner portions C) flank portion), the lower end of the body 32 has a stepped contour. That is, the leg portions 32a and the non-leg portions 32a' alternately occur.

Since the first body 32 is supported on the floor by the leg portions 32a, with the non-leg portions 32a' being spaced from the surface of the floor, the total height of the first body 32 depends on the height of the leg portions 32a. That is, the illumination distance is defined by the height of the leg portions 32a. Therefore, it is preferable that the leg portions 32a have a predetermined height (i.e. length) by which a sufficient illumination distance can be secured.

The non-leg portions 32a' are positioned to face each other, and the lower ends of the non-leg portions 32a' are spaced from the floor surface, thereby defining an opening in each side of the first body 32 when the first body 32 is placed on the floor.

Since the first body 32, as described above, is composed of the leg portions 32 and the non-leg portions 32a', in a case where the first body 32 is optionally provided underneath the cover 20, an illumination target object can be sterilized regardless of the size thereof. This will be described in detail below with reference to FIG. 6.

The first body 32 is formed to have a smaller horizontal area than the cover 20. The first body 32 is inserted into the second body 31. Thus, the first body 32 is formed to have a smaller horizontal area than the cover 20 and to have a smaller horizontal area than the second body 31.

As illustrated in FIG. 5, the second body 31 includes a bottom portion 34 and a wall portion 35 that extends upward from the bottom portion 34. In this case, the wall portion 35 constitutes a flank surface of the second body 31.

The second body 31 is formed to have the same horizontal area as, or a smaller horizontal area than, the cover 20. In FIG. 5, it is illustrated that the second body 31 is inserted into the housing 33 and that the second body 31 is formed to have a smaller horizontal area than the cover 20. Regardless of the presence or absence of the housing 33, the second body 31 may be formed to have a smaller horizontal area than, or the same horizontal area as the cover 20. However, preferably, the second body 31 is formed to have a smaller horizontal area than the cover 20 in a case where the housing 33 is provided, and is formed to have the same horizontal area as the cover 20 in a case where the housing 33 is not provided.

The second body 31 is open at the top and has the wall portion 35 and the bottom portion 34. That is, the second body 31 has a structure in the form of an open box. With this structure, in either a case where the body 30 composed of the first body 32 and the second body 31 is provided underneath the cover 20 or a case where only the second body 31 is provided underneath the cover 20, the sealed sterilization space S is formed within the UV sterilizer 1.

The body 30 is composed of the first body 32 and the second body 31 which are separably combined. Therefore, it is possible that only either one of or both of the first body 32 and the second body 31 are provided underneath the cover 20. In a case where the body 30 that results from combining the first and second bodies 32 and 31 is provided underneath the cover 20, the sealed sterilization space S is defined by the flank surfaces of the second body 31 and the cover 20, within the body 30.

With this structure, the advantage that the UV sterilizer 1 is convenient in terms of portability and mobility is provided. Specifically, in a case where the body 30 that results from combining the first and second bodies 32 and 31 is provided underneath the cover 20, or in a case where only the second body 31 is provided, a space within the UV sterilizer 1 is sealed by the wall portion 35 and the bottom portion 34 of the second body 31. With this structure, the UV sterilizer 1 effectively sterilizes the illumination target object 60 while being carried or moved with the illumination target object 60 to be sterilized placed within the UV sterilizer 1.

As illustrated in FIG. 5, a shape engagement portion 31a that is shape-engaged with the leg portions 32a and the non-leg 32a' of the first body 32 is formed in an internal wall 35 of the second body 31. In other words, the shape engagement portion 31a that is shape-engaged with the leg portions 32a and the non-leg portions 32a' of the first body 32 is formed in an internal flank surface of the second body 31.

With the shape engagement portion 31a, the first and second bodies 32 and 31 are combined with each other, and thus are provided, as the body 30, underneath the cover 20. The first body 32 is inserted into the second body 31, thereby being combined with the second body 31. Thus, a shape corresponding to the first body 32 is formed, in an engraved manner, in the internal flank surface of the second body 31. In other words, the shape corresponding to the first body 32 is formed, in an engraved manner, in the internal flank surface of the second body 31, thereby forming the shape engagement portion 31a.

With the shape engagement portion 31a, the first and second bodies 32 and 31 are combined with each other, and the sealed sterilization space S is formed, by the flank surfaces of the second body 31 and the cover 20 provided on the top of the body 30, within the body 30.

According to the present invention, with reference to FIG. 5, the first and second bodies 32 and 31 are described as being combined with each other with the shape engagement portion 31a. However, the first and second bodies 32 and 31 may be formed to be combined with each other using a different combination structure (for example, a structure in which the first body 32 is simply inserted into the second body 21).

The first and second bodies 32 and 31 are formed of metal material having the property of a high reflectance.

Accordingly, in a case where UV light is emitted from the illumination unit 10 into the body 30, a more effective sterilization process can be performed with a high reflectance.

The body 30 can be protected by the housing 33 into which the second body 31 thereof is inserted. In this case, the housing 33 is formed of resin material containing plastic. This makes it possible for the housing 33 to serve to protect the body 30. FIG. 4 illustrates that the housing 33 is provided. However, the housing 33 may be selectively provided.

The housing 33 is provided into which the second body 31 of the first and second bodies 32 and 31 that are combined with each other with the shape engagement portion 31a is inserted. In a case where only the first body 32 is provided, the housing 33 is provided into which the first body 32 is inserted, and thus serves to form the sealed sterilization space S within the body 30.

Figure 6:
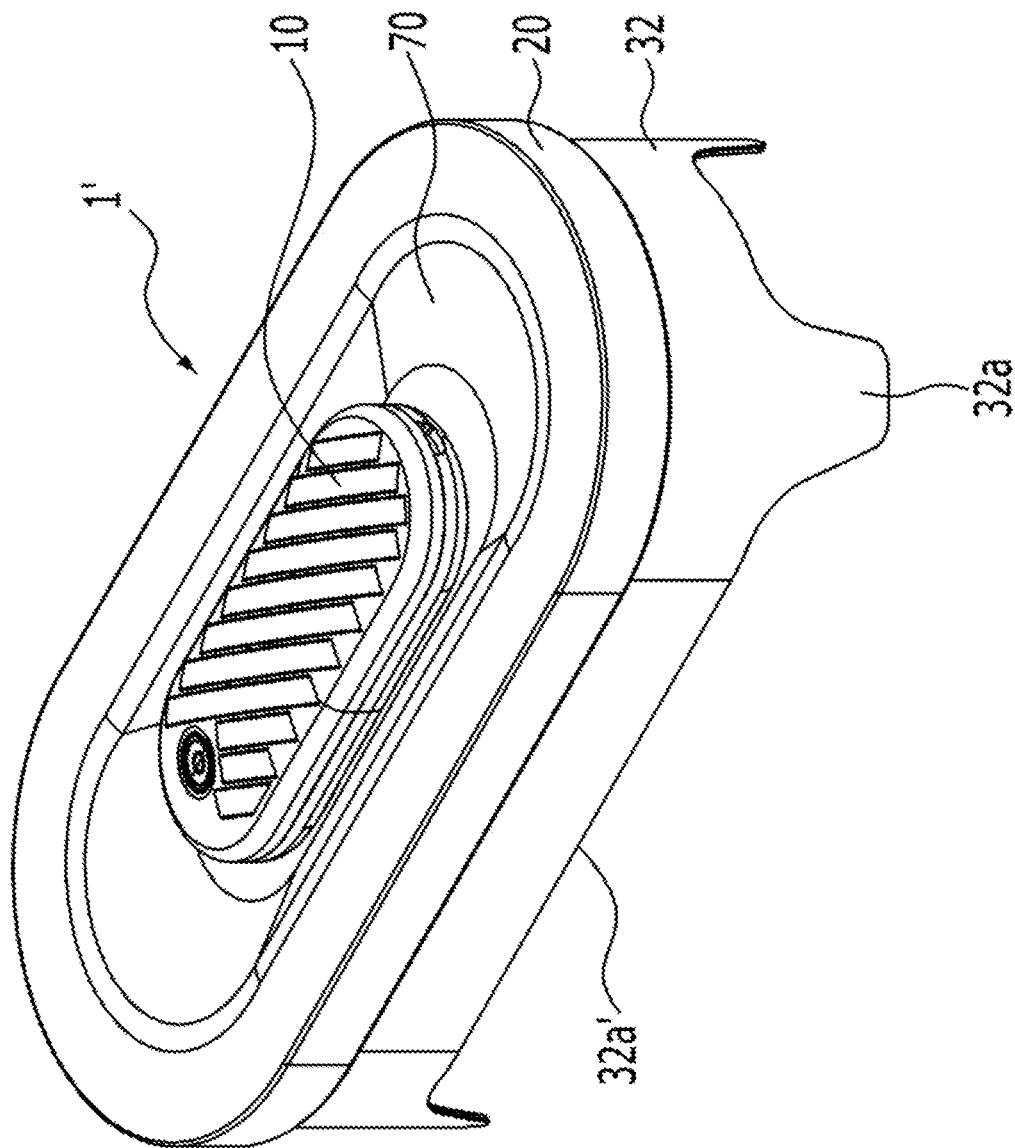
FIG. 6 is a diagram illustrating a state where a cover within which an illumination unit is nested and a first body are combined with each other.

According to the present invention, only the first body 32 is provided underneath the cover 20 within which the illumination unit 10 is nested, and thus various illumination target objects 60 can be sterilized regardless of the sizes thereof. This is described in detail with reference to FIG. 6. FIG. 6 is a diagram illustrating a state where the first body 32 is provided underneath the cover 20 within which the illumination unit 10 is nested.

As illustrated in FIG. 6, in a case where only the first body 32 is provided underneath the cover 20, the leg portion 32a and the non-leg portion 32a that constitute the first body 32 make it possible to sterilize various illumination target objects 60 regardless of the sizes thereof.

The non-leg portion 32a' of the first body 32 is formed to pass through the lower portion of the first body 32. Accordingly, in a case where only the first body 32 is provided underneath the cover 20, the sterilization space S that is partially open at each side thereof is defined by the non-leg portions 32a'.

Particularly, an illumination target object may not have a flat surface, may have a larger size than the second body 31, or may have a curved portion. The configuration of the first body 32 makes it possible to sterilize such an illumination target object.

The structure of the first body 32 makes it unnecessary to place the illumination target object considering the size of the sealed sterilization space formed by sealing a flank surface of the first body 32. Thus, products having various sizes, which are illumination target objects, can be sterilized regardless of the sizes thereof.

Figure 7:
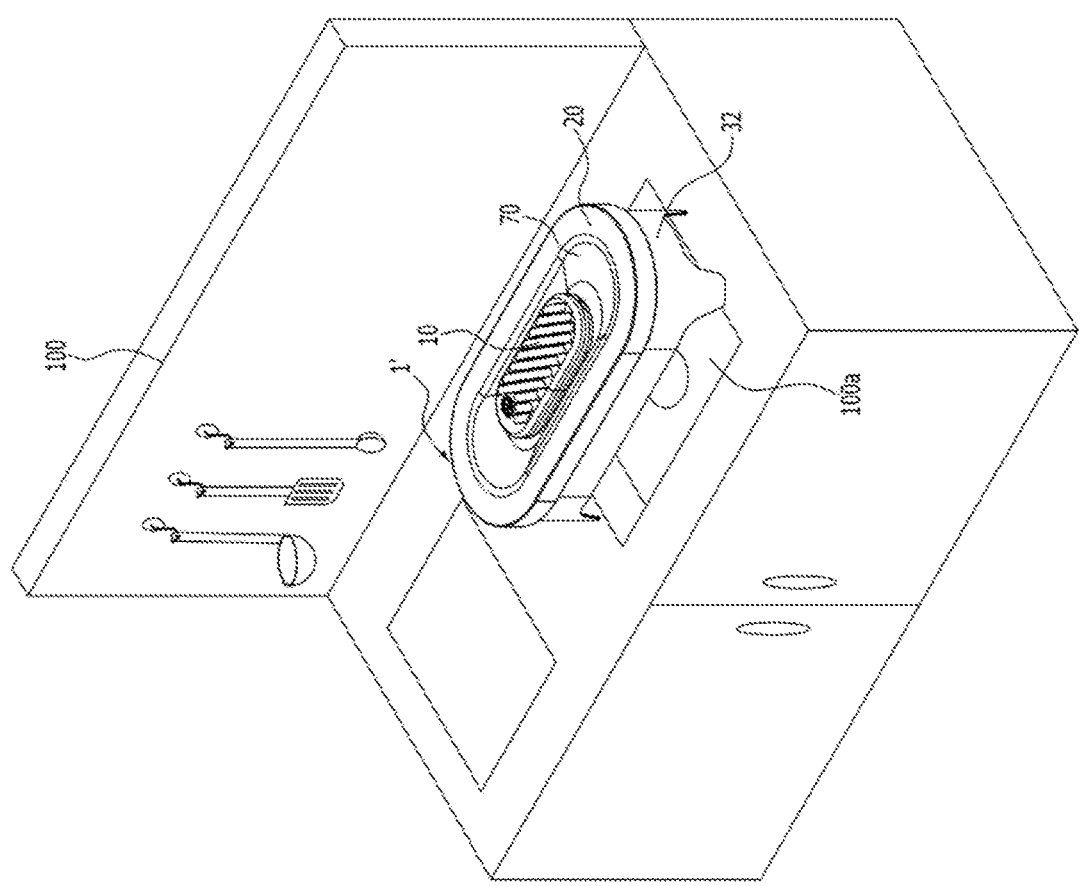
FIG. 7 is a diagram illustrating that a UV sterilizer according to an embodiment of the present invention sterilizes an illumination target object that has a larger size than the UV sterilizer.

FIG. 7 is a diagram illustrating that the UV sterilizer according to the present invention sterilizes an illumination target object that has a larger size than the UV sterilizer.

In this case, a UV sterilizer 1' includes only the first body 32 underneath the cover 20 within which the illumination unit 10 is nested.

FIG. 7 illustrates a toy kitchen 100 for a child, including a miniature sink 100a. Referring to FIG. 7, the UV sterilizer 1' will be described assuming that the miniature sink 100a is an illumination target object. The miniature sink 100a in the toy kitchen 100 has a larger size than the UV sterilizer 1'. In addition, the miniature sink 100a is an integral part of the toy kitchen 100. Thus, the miniature sink 100a cannot be separated from the toy kitchen 100 to place it within the UV sterilizer 1' for sterilization. Child toys can be washed with water. However, the miniature sink 100a has a larger size than small-sized toys, such as a miniature vehicle and thus is difficult to wash frequently. In addition, it is difficult to remote bacteria growing on a large-sized toy such as the toy kitchen 100 with only washing. Thus, for sterilization, it is necessary to use a sterilizer.

However, a UV sterilizer having a larger size than a sterilization target object is difficult to secure in order to sterilize a large-size product, such as the large-sized toy kitchen 100, when considering a purchase cost.

However, regardless of its size, an illumination target object that, for example, is the entire toy kitchen 100 can be sterilized with the UV sterilizer 1' according to the present invention having a structure in which only the first body 32 is provided underneath the cover 20 within which the illumination unit 10 is nested. As illustrated in FIG. 7, the UV sterilizer 1' is placed on the top of the miniature sink 100a of the toy kitchen 100. In this case, the first body 32 primarily serves to secure the illumination distance between the illumination unit 10 and the miniature sink 100a.

The UV sterilizer 1' in which the illumination distance for achieving a high uniformity ratio of illumination is secured has the open sterilization space S of which the flank side is made to be open by the non-leg portion 32a'. Thus, the miniature sink 100a does not need to be separated from the toy kitchen 100 and to be placed within the UV sterilizer 1'. Instead, the UV sterilizer 1' is placed on the top of the miniature sink 100*a*. Then, an area where the miniature sink 100*a* is present is illuminated with UV light.

In this manner, the UV sterilizer 1' has the uniformity ratio of illumination improved by the first body 32. The UV sterilizer 1', when placed on the top of the illumination target object, can sterilize the illumination target object 100*a* having a larger size than the UV sterilizer 1'. In order to sterilize the entire toy kitchen 100, the UV sterilizer 1' is moved to an area other than the area where the first-sterilized miniature sink 100*a* is present.

As described above, the UV sterilizers 1 and 1' according to the present invention selectively have configurations of the body 30 and thus employ a structure in which sterilization effective in terms of portability and mobility is possible. In addition, the UV sterilizers 1 and 1' may employ structures for sterilizing products having various sizes, which are sterilization target objects, regardless of the sizes thereof.

In addition, the body 30 is formed in such a manner as to employ a structure in which the uniformity ratio of illumination is improvable. Although the body 30 is separated into smaller portions, the UV sterilizer can provide the effect of achieving a high uniformity ratio of illumination.

In this manner, each of the UV sterilizers 1 and 1' according to the present invention has a structure that varies according to the employed configuration. With one UV sterilizer, products having various sizes can be sterilized according to the sizes thereof. In other words, by changing the structure of the UV sterilizer, products can be sterilized regardless of the sizes thereof.

The preferable embodiment of the present invention is described above, and it is apparent to a person of ordinary skill in the art that various modifications and alterations to the present invention are possibly implemented within the scope that does not depart from the subject matters of the present invention that are defined in the following claims.

What is claimed is:

1. a body that is provided underneath the cover and secures an illumination distance between the illumination unit and an illumination target object, wherein the body is composed of a first body and a second body into which the first body is inserted, and the first body and the second body are separably combined with each other, wherein the first body and the second body are separated from each other and are selectively provided underneath the cover, wherein the first body includes a leg portion and a non-leg portion, the non-leg portion being shorter in length than the leg portion thereby forming an opening at a side of the first body, the opening passing through a lower portion of the first body, wherein the leg portion is configured to support the first body on a floor, and the leg portion has a predetermined height to secure the illumination distance, wherein the second body includes a shape engagement portion that is shape engaged with the leg portion and the non-leg portion of the first body, the shape engagement portion being formed in an internal wall of the second body, and wherein the first body is inserted into the second body, and the first body and the second body are separably combined with each other by the shape engagement portion.

2. The UV sterilizer according to claim 1, wherein a sealed sterilization space is formed, by the internal wall of the second body and the cover, within the body.

3. The UV sterilizer according to claim 1, wherein the cover includes a nesting portion within which the illumination unit is nested.

4. The UV sterilizer according to claim 1, wherein the non-leg portion has a lower end that is spaced apart from the floor to define the opening at the side of the first body, when the first body is supported on the floor.

5. The UV sterilizer according to claim 1, wherein the shape engagement portion is engraved on an internal side surface of the second body.

* * * * *